(12) United States Patent
Mace et al.

(10) Patent No.: US 7,004,168 B2
(45) Date of Patent: Feb. 28, 2006

(54) FACE MASK FOR GAS MONITORING DURING SUPPLEMENTAL OXYGEN DELIVERY

(75) Inventors: Leslie E Mace, Mercer Island, WA (US); David R Rich, Glastonbury, CT (US); Randall J Terry, Wallingford, CT (US); John A Triunfo, Jr., Fairfield, CT (US); Anthony T Pierry, Plantsville, CT (US); Michael J. R. Polson, South Pembrokeshire (GB)

(73) Assignee: Respironics, Inc., Murrysville, PA (US)

( * ) Notice: Subject to any disclaimer, the term of this patent is extended or adjusted under 35 U.S.C. 154(b) by 64 days.

(21) Appl. No.: 10/230,502

(22) Filed: Aug. 29, 2002

(65) Prior Publication Data

US 2003/0047188 A1   Mar. 13, 2003

Related U.S. Application Data

(60) Provisional application No. 60/318,212, filed on Sep. 7, 2001.

(51) Int. Cl.
*A62B 18/02* (2006.01)

(52) U.S. Cl. .......................... 128/206.21; 128/203.12; 128/204.22; 128/205.11; 128/205.24; 128/206.28; 600/532; 600/538

(58) Field of Classification Search .......... 128/201.24, 128/203.12, 203.14, 203.16, 203.22, 203.23, 128/203.25, 203.29, 204.18, 204.21, 204.22, 128/204.26, 205.11, 205.25, 206.12, 206.15, 128/206.21–207.18, 201.18, 203.21, 204.19, 128/200.14–200.24, 205.23, 204.23; 600/529, 600/532, 533, 537, 538–543
See application file for complete search history.

(56) References Cited

U.S. PATENT DOCUMENTS

| | | | |
|---|---|---|---|
| 4,011,865 A | 3/1977 | Morishita | |
| 5,046,491 A | 9/1991 | Derrick | |
| 5,857,460 A * | 1/1999 | Popitz | 128/206.21 |
| 5,868,133 A * | 2/1999 | DeVries et al. | 128/204.21 |
| 6,192,884 B1 | 2/2001 | Vann et al. | |
| 6,247,470 B1 | 6/2001 | Ketchedjian | |

(Continued)

OTHER PUBLICATIONS

Loughnan et al., "A Comparison of Carbon Dioxide Monitoring and Oxygenation Between Gacemask and Divided Nasal Cannula", Anaesth Intensive Care 2000, Apr. 2000, Pp. 151-154, vol. 28.

Waldau et al., "The Effect of Nasal Oxygen Flow and Catheter Position on the Accuracy of Eng-Tidal Carbon Dioxide Measurements by a Pharyngeal Catheter in Unintubated, Spontaneously Breathing Subjects", Anaesthesia, 1995, Pp. 695-698, vol. 50, The Association of Anaesthetists of Gt. Britain and Ireland.

Ivens, et al., "The Quality of Breathing and Capnography During Laryngeal Mask ad Facemask Ventilation", Anaesthesia, 1995, Pp. 858-862, vol. 50, The Association of Anaesthetists of Gt. Britain and Ireland.

*Primary Examiner*—Glenn K. Dawson
(74) *Attorney, Agent, or Firm*—Michael W. Haas

(57) ABSTRACT

A face mask including a gas monitoring capability for improved patient management in combination with improved efficiency of supplemental oxygen delivery to the patient is provided. The face mask of the present invention is configured to direct substantially all of the inspiratory and expiratory gas streams to and from the patient through a gas measuring device and to efficiently deliver supplemental oxygen. As such, the face mask permits measurement of both oral and nasal gas exchange.

17 Claims, 5 Drawing Sheets

U.S. PATENT DOCUMENTS

| | | |
|---|---|---|
| 6,306,099 B1 | 10/2001 | Morris |
| 6,402,697 B1 | 6/2002 | Calkins et al. |
| 6,599,252 B1 * | 7/2003 | Starr .......................... 600/532 |
| 2002/0174866 A1 * | 11/2002 | Orr et al. ............... 128/200.24 |

* cited by examiner

FACE MASK FOR GAS MONITORING DURING SUPPLEMENTAL OXYGEN DELIVERY

CROSS REFERENCE TO RELATED APPLICATIONS

Under the provisions of 35 U.S.C. § 119(e), this application claims the benefit of U.S. Provisional Application Ser. No. 60/318,212, filed Sep. 7, 2001, the contents of which are hereby incorporated by reference herein as if set forth in their entirety.

BACKGROUND OF THE INVENTION

1. Field of Invention

The present invention relates generally to gas monitoring techniques and apparatus. More specifically, the present invention relates to a method and apparatus for monitoring the respiratory gases of spontaneously breathing patients who are receiving supplemental oxygen.

2. Description of the Related Art

Supplemental oxygen is widely used for the long-term treatment of chronically ill patients suffering from various respiratory diseases such as Chronic Obstructive Pulmonary Disease (COPD) and emphysema. Additionally, in emergency situations, supplemental oxygen is administered on a short-term basis to relieve acute symptoms, such as shortness of breath and lowered oxygen saturation. Supplemental oxygen is also commonly administered throughout the hospital setting, such as in the operating room during surgery and post-op, and in the intensive care units to critically ill patients.

Conventional practices for administering supplemental oxygen to a patient include nasal cannulae and face masks. The nasal cannula consists of tubing with a pair of stubs that are situated within the nostrils of the patient and through which oxygen flows. The nasal cannula provides more freedom of movement for the patient than other methods but drawbacks of using the nasal cannula are well known and include unknown delivered $FIO_2$ (fraction of inspired oxygen), irritation of the nose and easy dislodgment of the cannula from the patient's nostrils. Moreover, cannulae including a gas monitoring capability exhibit a recognized inability to detect both oral and nasal gas exchange as well as a tendency to dilute the measured gas.

A nasal cannula design that purportedly overcomes the nasal irritation problem and reduces the potential for easy dislodgment from the nostrils is disclosed in U.S. Pat. No. 6,247,470 (hereinafter "the '470 Patent"), issued to Ketchedjian on Jun. 19, 2001. The '470 patent uses a flexible and adjustable lever arm placed with its free end adjacent the patient's mouth to direct oxygen toward the user's oral and nasal cavities and to intake exhaled $CO_2$ for monitoring purposes. Thus, the device is similar in configuration to a telephone headset for hands-free speaking.

While this device is not subject to nasal dislodgment, with its unwieldy fixation scheme it is subject to easy spatial relocation, potentially dramatically reducing the efficiency of the oxygen delivery. Further, a clinical study published by Bazuaye (Bazuaye E A et al. *Variability of inspired oxygen concentration with nasal cannulas. Thorax.* 1992 Dec; 47(12): 1086) concludes that "'Typical' values of $FIO_2$ quoted with nasal cannulas can mislead . . . confirm(ing) that this mode of oxygen delivery is unsatisfactory if precise control of inspired oxygen is desired." Thus, while the apparatus of the '470 patent provides a monitoring capability combined with oxygen delivery, its inefficient delivery in comparison to face masks and the unenclosed gas sampling location relatively distant from oral and nasal cavities makes this apparatus of questionable clinical utility.

Oxygen delivery cannulae incorporating a sidestream $CO_2$ monitoring capability such as the NAZORCAP™ sampler offered by NAZORCAP Medical, Inc. of West Mifflin, Pa. and further described in U.S. Pat. No. 5,046,491, issued to Derrick on Sep. 10, 1991, also have a number of drawbacks. For instance, such oxygen delivery cannulae exhibit problems with moisture and mucous plugs, switching back and forth between oral and nasal breathing, and dilution of $CO_2$ readings with administered $O_2$.

Oxygen masks, which are simple, inexpensive to use, and not subject to easy dislodgment, have also been employed to reliably administer oxygen levels of 40–60% $O_2$ to the patient. Oxygen mask designs vary based upon intended use of the particular mask. Oxygen masks include a body that is sized to seat over the nose and mouth of the patient on whom the mask is to be placed. With conventional mask designs, oxygen is introduced through an oxygen inlet, and expiratory gases are vented from the mask through apertures.

Disadvantages of conventional oxygen mask delivery systems include wasted oxygen because the oxygen flow continues unabated directly into the mask during exhalation and could be more efficiently delivered to the patient. Depending upon the mask design, the patient may not tolerate a mask for more than short periods of time. Also, no quantitative monitoring of the end-tidal carbon dioxide is performed. Such monitoring would allow for the diagnosis of hypercapnia, which indicates inadequate oxygen delivery and the need for a more aggressive treatment strategy.

While recent designs have addressed these disadvantages of wasted oxygen and gas measurement separately, an apparatus providing for better titration of oxygen to the patient would be advantageous.

One design that purportedly provides enhanced efficiency of oxygen use was recently disclosed in U.S. Pat. No. 6,192,884, issued to Vann et al. on Feb. 27, 2001. The enhanced efficiency is described as relating to the administration of an oxygen bolus at the beginning of each inhalation by a patient.

A mask design with a qualitative calorimetric sensor that purportedly senses the presence or absence of carbon dioxide and is integral and in intimate contact with the mask housing was disclosed in U.S. Pat. No. 5,857,460 (hereinafter "the '460 Patent"), issued to Popitz et al. on Jan. 12, 1999. However, the device of the '460 Patent is not positioned in the respiratory gas stream and, as such, only assesses the presence or absence of carbon dioxide and provides only information that is, at best, qualitative.

Thus, recent designs have attempted to separately address the problems of wasted oxygen and gas measurement. However, a design which addresses them in combination to promote better titration of oxygen to the patient would be desirable.

A type of patient sedation termed "conscious sedation" has been recognized as advantageous for certain types of surgical and diagnostic procedures and is becoming ever more prevalent. This sedation type induces an altered state of consciousness that can minimize pain and discomfort through the use of pain relievers and sedatives. Patients who receive conscious sedation are usually able to speak out and respond to verbal cues throughout a procedure, enabling them to communicate any discomfort they experience to the health care provider. A brief period of amnesia may subsequently erase any memory of the procedure. Further, conscious sedation allows patients to recover quickly and resume normal daily activities in a short period of time.

Conscious sedation provides a safe and effective option for patients undergoing minor surgical or diagnostic procedures. The number and types of procedures that can be performed using conscious sedation have increased significantly as a result of new technology and state of the art pharmaceuticals. Exemplary procedures with which conscious sedation is useful include breast biopsy, vasectomy, minor foot surgery, minor bone fracture repair, plastic or reconstructive surgery, dental prosthetic or reconstructive surgery, and endoscopy, such as for diagnostic studies and treatment of stomach, colon and bladder.

Non-intubated gas exchange monitoring of the sedated, conscious patient is necessary because patients can slip into a deep sleep. However, conventional techniques as described above afford inadequate monitoring capability to the clinician.

SUMMARY OF THE INVENTION

The present invention provides a face mask including a gas monitoring capability for improved patient management in combination with improved efficiency of supplemental oxygen delivery to the patient.

The face mask of the present invention is configured to direct substantially all of the inspiratory and expiratory gas streams to and from the patient through a gas measuring device and to efficiently deliver supplemental oxygen. As such, contrary to nasal cannulae, the face mask allows measurement of both oral and nasal gas exchange.

The supplemental oxygen delivery inlet is located so that it does not mix with the expiratory gases prior to their measurement but is still available to enrich the gas stream during inhalation. The avoidance of expiratory gas mixing is accomplished by locating the oxygen delivery inlet distal to the gas measurement component in mainstream arrangements or distal to the sampling site in the case of a sidestream arrangement. This avoids dilution of the expiratory gases by the delivered oxygen and allows a capnograph to accurately measure end-tidal $CO_2$ of the patient as well as other gases, including, without limitation, $O_2$. Measurement of $O_2$ allows better control of titrated gas as well as provides valuable diagnostic information. A fixed or, optionally, an adjustable or expandable corrugated hose associated with the oxygen delivery inlet provides a reservoir of oxygen for the next inhalation. Provided the flow rate of oxygen is sufficient, the added volume of the reservoir will not result in significant $CO_2$ rebreathing. Thus, the portion of the inspiratory gases within this reservoir will not contain the gases from the end of exhalation as with conventional rebreathing systems but instead contain primarily end-expiratory gas diluted with 100% $O_2$.

Unlike conventional oxygen delivery systems, the mask of the present invention is imperforate and does not contain any additional apertures or valves for venting the expiratory gases. Because one purpose of the face mask of the present invention is to provide accurate gas monitoring, a good seal between the peripheral rim of the mask and the patient's face is effected to prevent dilution of the inspiratory gases by ambient gases. Thus, the gas measuring device associated with the face mask is enabled to provide quantitative information on the expiratory gases such as end-tidal values and respiratory rate as well as qualitative values.

The present invention contemplates that some configurations of the gas measuring device include a flow measuring component to allow flows and volumes to be quantitatively assessed to determine the need for additional medical care. Alternatively, a valving scheme using a Y or T piece may be used. Appropriately oriented one-way check valves on each limb of the Y or T piece may be used to direct gas flow through the appropriate limb depending upon the phase (i.e., inhalation or exhalation) of the patient's respiratory cycle. Also, the face mask of the present invention is configured with minimal dead space within the mask volume as placed on the patient to more accurately reflect the patient's carbon dioxide output, but is otherwise of conventional construction.

In one embodiment of the face mask of the present invention, the oxygen reservoir is distally located from the oxygen delivery inlet while in another embodiment the oxygen delivery inlet is located distally from the reservoir.

One significant advantage of the present invention is that it enables effective detection of both oral and nasal gas exchange without dilution enabling, among other capabilities, an accurate measurement of end tidal $CO_2$.

Further, $O_2$ measurement combined with a flow sensor allows measurement of gas exchanges such as $CO_2$ elimination and oxygen consumption as well as calculation of measures such as resting energy expenditure and respiratory quotient.

The present invention is particularly suitable for nonintubated gas exchange monitoring of conscious sedation patients, although the invention is not so limited.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

The present invention is directed to a face mask including a gas monitoring capability for improved patient management in combination with improved efficiency of supplemental oxygen delivery to a patient. The particular embodiments described herein are intended in all respects to be illustrative rather than restrictive. Alternative embodiments will become apparent to those of ordinary skill in the art to which the present invention pertains without departing from its scope.

Figure 1A:
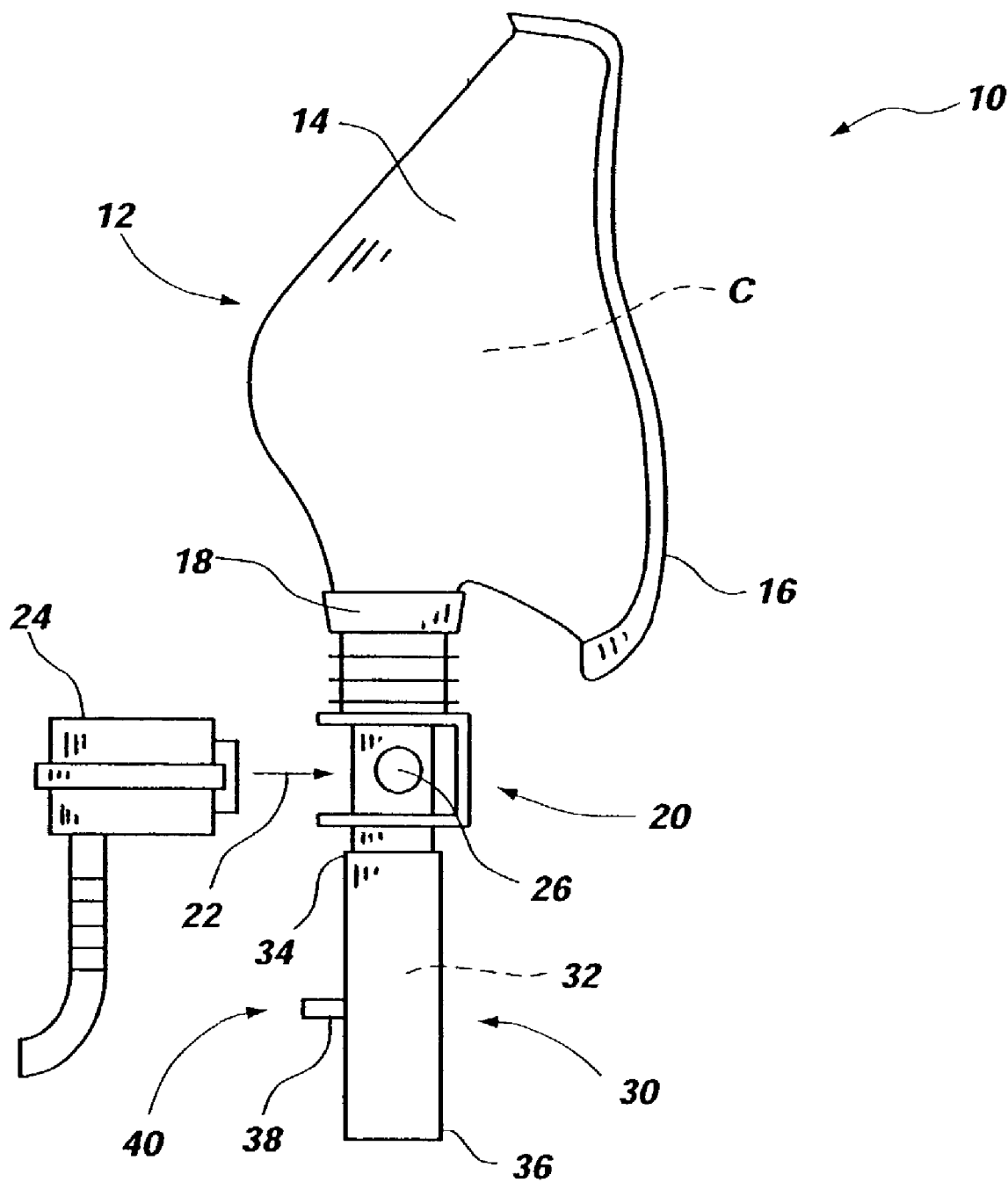
FIG. 1A is a side view of one embodiment of the face mask assembly of the present invention depicting a mainstream gas measurement device and one oxygen inlet delivery arrangement.
Figure 1B:
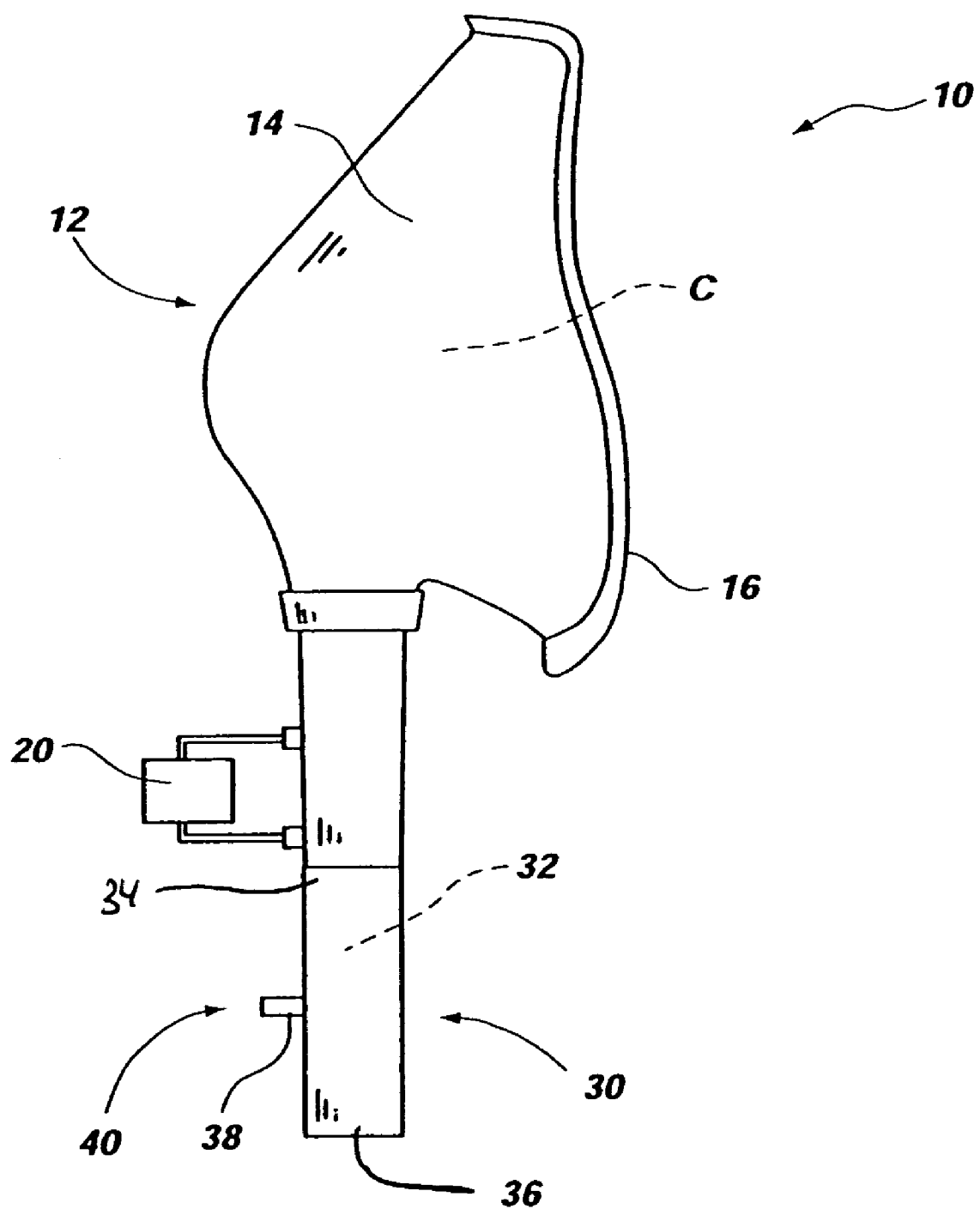
FIG. 1B is a side view of an embodiment of the face mask assembly of the present invention similar to FIG. 1A but depicting a sidestream gas measurement device.
Figure 2:
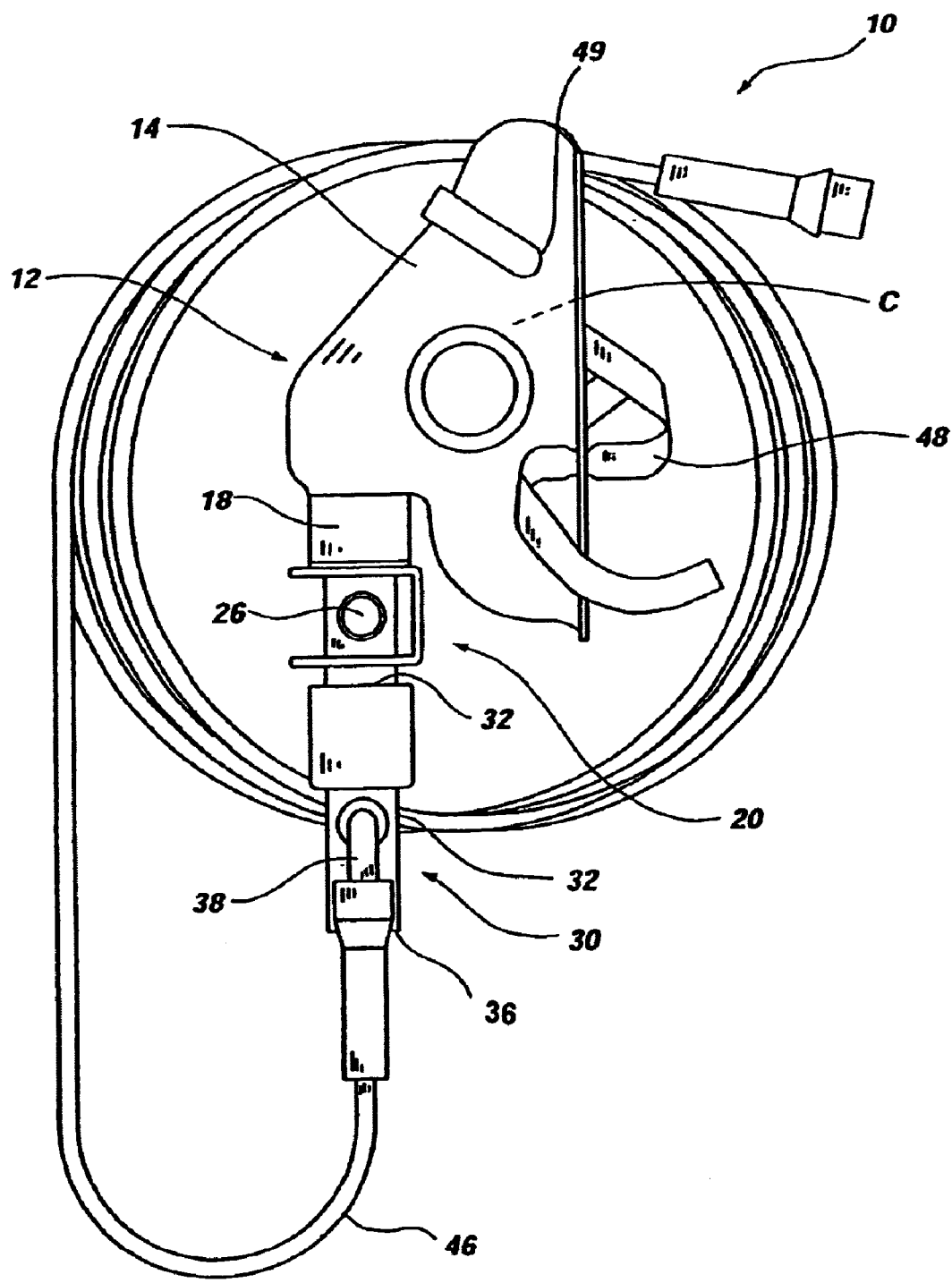
FIG. 2 is a side view of an embodiment of the face mask assembly of the present invention depicting an oxygen inlet delivery arrangement having a tube coupled therewith for conveying oxygen from a source.

Referring to the figures in general, and initially to FIGS. 1A, 1B, and 2 in particular, an exemplary embodiment of the face mask assembly according to the present invention is illustrated and denoted generally by reference numeral 10. The illustrated face mask assembly 10 includes a face mask 12 having a sheath or shell 14 defining a chamber C therein bounded by a flexible, compliant peripheral rim 16 for sealing against the face of a patient.

Face mask 12 further includes a port 18 by which face mask 12 is operably coupled to the proximal end of a gas measurement component in the form of gas sample cell 20. Gas sample cell 20 may be configured as part of a mainstream airway adapter (FIG. 1A) as shown, or as a sidestream sampling adapter (FIG. 1B). FIG. 1B illustrates a sidestream sampling system in which the sampled gas is returned to the mainstream airway adapter. It is to be understood, however, that the present invention contemplates using a sidestream sampling system in which the sampled gas is not returned to the mainstream airway adapter, but is vented to atmosphere.

Figure 5:
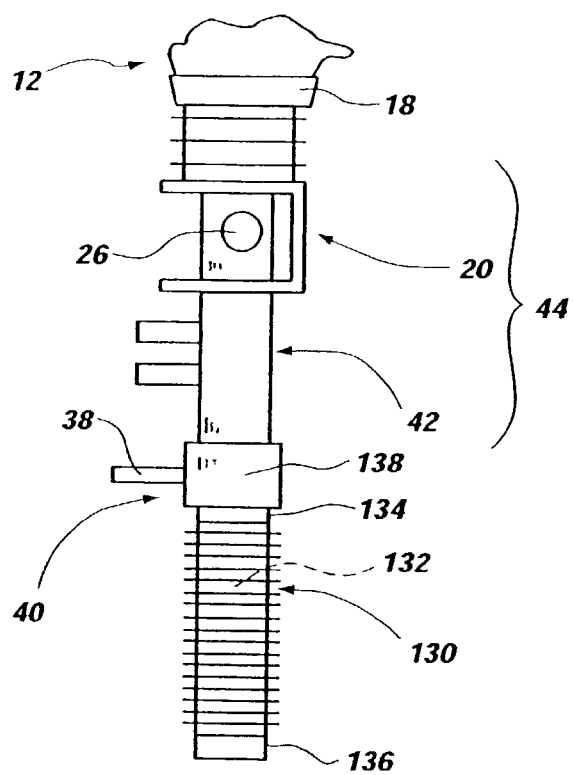
FIG. 5 is a side view of a portion of the face mask assembly of the present invention similar to that of FIG. 2 having a gas measurement device and further including a flow measurement capability.

Additionally, gas sample cell 20 may be combined with, or optionally include, a flow measurement component 42 as shown in FIG. 5 and further described with respect thereto. As shown by arrow 22 of FIG. 1A, a removable mainstream gas sensor 24 may be placed over gas sample cell 20 to optically sense through opposed aligned windows 26, one or more constituents of respiratory gas flowing through gas sample cell 20. Though not shown, a gas sensor also may be placed over a sidestream sample cell, such as that depicted in FIG. 1B. One suitable $CO_2$ gas sensor is the CAPNOSTAT brand of infrared (IR) sensor offered by Respironics Novametrix of Wallingford, Conn. The proximal end of an oxygen delivery chamber 30 is operably coupled to the distal end of the gas sample cell 20.

An oxygen delivery housing 30 defines a reservoir 32 having open proximal and distal ends 34 and 36 by which oxygen delivery housing 30 is respectively operably coupled to the distal end of gas sample cell 20 and open to the ambient atmosphere. An oxygen delivery inlet port 38 is defined by a nipple 40 (FIGS. 1A and 1B) opening into reservoir 32 from the midsection of housing 30 and to which a tube 46 (FIG. 2) for conveying oxygen from a source may be coupled. Reservoir 32 may be of fixed volume, as shown in FIGS. 1A and 1B, or variable volume as depicted and discussed hereinafter in more detail with respect to FIGS. 3 and 4. A flexible strap 48 may be coupled to face mask 12 by strap apertures (see FIG. 2). Alternatively, other means as known in the art may be used to secure face mask 12 in substantial sealing engagement by peripheral rim 16 with the face of the patient, such as providing an adhesive about peripheral rim 16.

Figure 3:
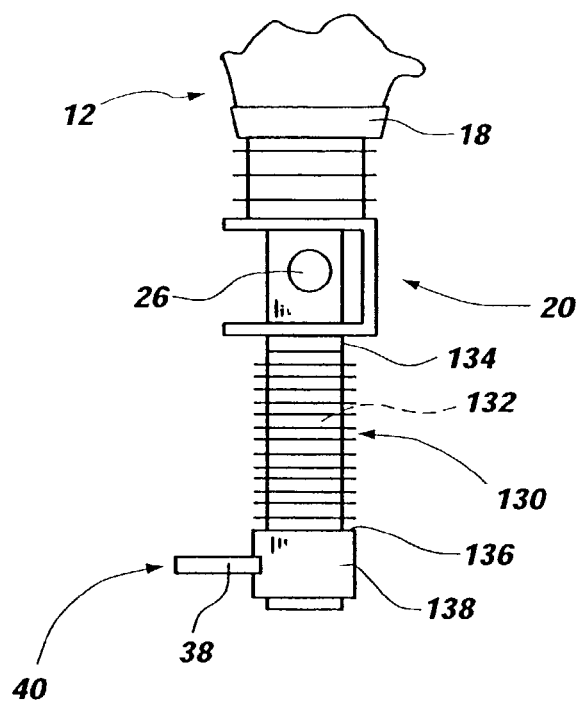
FIG. 3 is a side view of a portion of the face mask assembly of the present invention depicting a first variation of an oxygen delivery inlet arrangement with adjustable volume reservoir.
Figure 4:
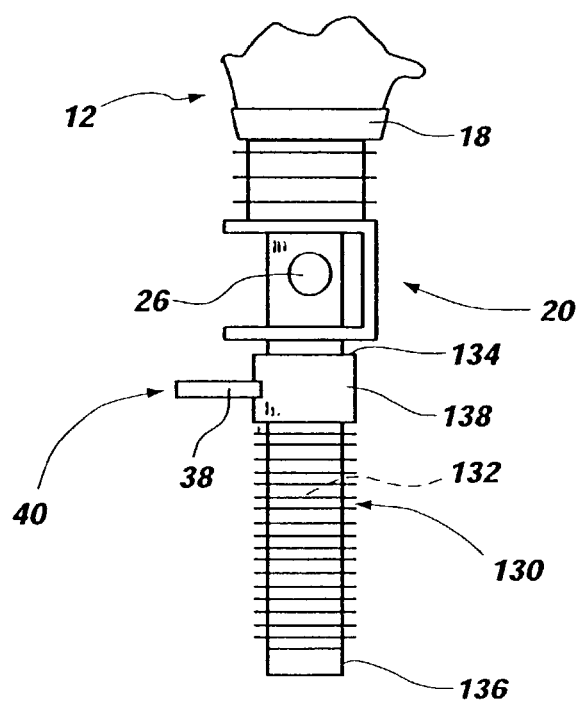
FIG. 4 is a side view of a portion of the face mask assembly of the present invention depicting a second variation of an oxygen delivery arrangement with adjustable reservoir volume.

FIGS. 3 and 4 show a portion of face mask 12 with gas sample cell 20 and variations of the oxygen delivery inlet arrangement of FIG. 1. In the variation of FIG. 3, oxygen delivery inlet port 38 and nipple 40 are near a distal end 136 of the length of an adjustable volume oxygen delivery housing 130 defining a variable or adjustable volume reservoir 132. Adjustable volume oxygen delivery housing 130 may be, for example, a corrugated length of tubing or a telescoping tube. In either instance the volume of reservoir 132 is adjustable.

In the variation of FIG. 4, on the other hand, the oxygen delivery inlet port 38 and nipple 40 are placed near a proximal end 134 of adjustable volume oxygen delivery housing 130. The variation of FIG. 4 is currently preferred because this approach provides a more effective storage capability for the delivered $O_2$ and washout of end-expiratory gas by placing reservoir 132 distally of oxygen delivery port 38 and nipple 40.

The embodiment in FIG. 5 shows a configuration similar to that of FIG. 4, but wherein a gas sample cell 20 is combined with a differential pressure type flow measurement component 42 similar to those disclosed and claimed in U.S. Pat. No. 5,879,660 (1998) to Kofoed, et al. to form a combined gas and flow measurement component 44. Of course, a discrete gas sample cell may be combined with a discrete flow measurement component in a combined gas and flow measurement assembly. Further, flow measurement may be effected by any technique known in the art, and is not limited to differential pressure measurement.

FIG. 5 depicts the oxygen delivery inlet port 38 and nipple 40 placed near proximal end 134 of adjustable volume oxygen delivery housing 130. However, it will be understood and appreciated by those of ordinary skill in the art that oxygen delivery inlet port 38 and nipple 40 may be positioned near distal end 136 of the length of adjustable volume oxygen delivery housing 130 in an embodiment similar to the depiction of such elements in FIG. 3. Such variation is contemplated to be within the scope hereof.

If desired, an $O_2$ mainstream sensor (not shown) may be combined with a flow measurement component 42. An $O_2$ mainstream sensor, when combined in this manner, may provide more accurate $O_2$ administration.

Figure 6:
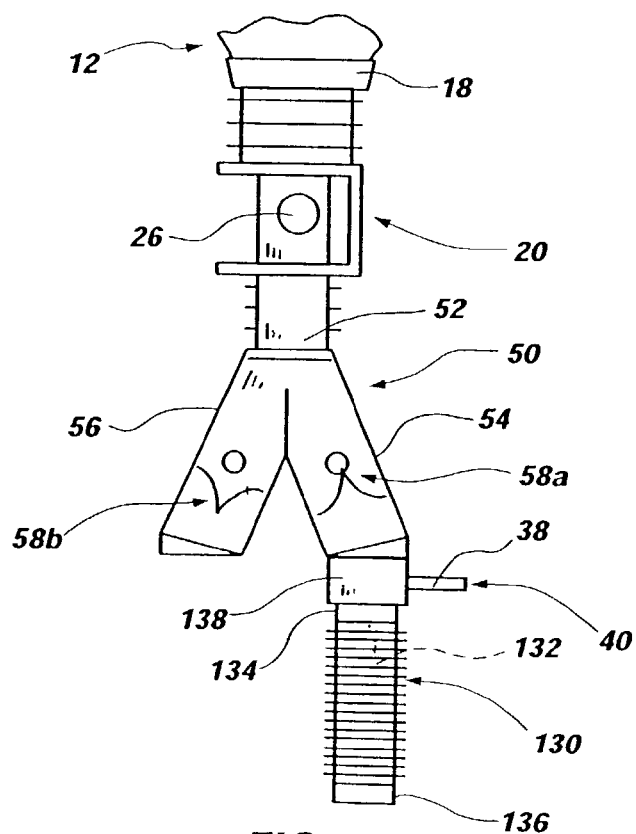
FIG. 6 is a side view of a portion of the face mask assembly of the present invention including a gas measurement device and a Y piece distal therefrom that includes check valves.

FIG. 6 shows a gas sample cell 20 operably coupled to a base 52 of a Y-adapter 50. Y-adapter 50 has two side legs 54 and 56, within which oppositely oriented unidirectional check valves 58a and 58b are respectively located so as to appropriately direct the gas flow. Leg 54 is operably coupled to an adjustable volume oxygen delivery housing 130 having oxygen delivery inlet port 38 and nipple 40 at the proximal end thereof. Check valve 58a is oriented to permit proximal flow of ambient atmospheric gas and supplemental oxygen to the patient and prevent distal flow of exhaled gases, while check valve 58b in leg 56 is oriented to block proximal flow of ambient atmospheric gas and permit distal flow of exhaled gases. It is also contemplated that adapter 50 may be configured as a T instead of a Y.

As shown in FIGS. 3 through 6, oxygen delivery inlet port 38 with nipple 40 may be configured as opening into a collar 138 at one end of oxygen delivery housing 130. Thus, as oxygen delivery housing 130 is reversed distally to proximally to form the configurations of FIGS. 3 and 4. Collar 138 may be coupled to a gas measurement component or be at a distal, open end of the face mask assembly 10.

In operation, the face mask of the present invention traps $CO_2$ upon exhalation (whether oral, nasal or combined) and pressure forces it out of the mask. Upon inhalation, ambient air is easily entrained into the face mask. This bi-directional gas exchange allows the attached gas ($CO_2$) sensor (FIG. 1) to easily track the patient's capnogram while avoiding problems attendant to sampling systems. Heat from the gas sensor substantially reduces the condensation in the gas sample cell. Further, the presence of the reservoir in the face mask of the present invention proximate the location of oxygen delivery reduces the amount of oxygen which might be wasted (not inspired by the patient) and provides it for the next inspiration.

While the face mask assembly of the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A face mask assembly, comprising:
    (a) a face mask sized and configured to fit over an oral region, a nasal region, or both of a user's face, the mask having a port;
    (b) a first conduit having a proximal end and a distal end, wherein the proximal end of the first conduit is coupled to the face mask through the port;
    (c) a gas sample cell defined in the first conduit;
    (d) a second conduit having a proximal end and a distal end, wherein the proximal end of the second conduit is coupled to the distal end of the first conduit such that the face mask, the first conduit, and the second conduit are supported on such a user during use of the face mask assembly, and wherein the distal end of the second conduit is open to ambient atmosphere, and wherein the second conduit includes a reservoir defined therein; and
    an oxygen port defined in a wall of the second conduit and adapted to communicate a source of oxygen with the reservoir.

2. The face mask assembly of claim 1, wherein the first conduit further comprises a gas sensor cooperatively coupled to the gas sample cell.

3. The face mask assembly of claim 1, wherein the reservoir is a fixed volume reservoir.

4. The face mask assembly of claim 3, wherein the oxygen port is located substantially medially along a length of the second conduit.

5. The face mask assembly of claim 3, wherein the oxygen port is located relatively proximally along a length of the second conduit.

6. The face mask assembly of claim 3, wherein the oxygen port is located relatively distally from the face mask along a length of the second conduit.

7. The face mask assembly of claim 1, further including a flow measurement component interposed between the face mask and the second conduit.

8. The face mask assembly of claim 7, wherein the flow measurement component is integral with the gas sample cell.

9. The face mask assembly of claim 1, further including structure for securing the face mask over the oral and nasal region of the patient's face.

10. A face mask assembly, comprising:
    (a) a face mask sized and configured to fit over an oral region, a nasal region, or both of a patient's face, the mask having a port;
    (b) a gas measurement component having a proximal end operably coupled to the face mask through the port; and
    (c) an oxygen delivery housing coupled to a distal end of the gas measurement component such that the gas measurement component and the oxygen delivery housing are connected proximate to the face mask, wherein the oxygen delivery housing includes:
        (1) a reservoir defined in the housing wherein the reservoir is an adjustable volume reservoirs,
        (2) an oxygen delivery inlet port opening into the housing, and
        (3) a primary fluid flow port opening into the reservoir, wherein the primary fluid flow port communicates the reservoir with an ambient atmosphere such that in use, a user breathes through the gas measurement component and the oxygen delivery housing.

11. The face mask assembly of claim 10, wherein the oxygen delivery inlet port is located medially along a length of the oxygen delivery housing.

12. The face mask assembly of claim 10, wherein the oxygen delivery inlet port is located relatively proximally along a length of the oxygen delivery housing.

13. The face mask assembly of claim 10, wherein the oxygen delivery inlet port is located relatively distally along a length of the oxygen delivery housing.

14. A face mask assembly, comprising:
    (a) a face mask sized and configured to fit over an oral region, a nasal region, or both of a patient's face, the mask having a port;
    (b) a gas measurement component having a proximal end operably coupled to the face mask through the port; and
    (c) an oxygen delivery housing coupled to a distal end of the gas measurement component such that the gas measurement component and the oxygen delivery housing are connected proximate to the face mask, wherein the oxygen delivery housing includes:
        (1) a reservoir defined in the housing,
        (2) an oxygen delivery inlet port opening into the housing, and
        (3) a primary fluid flow port opening into the reservoir, wherein the primary fluid flow port communicates the reservoir with an ambient atmosphere such that in use, a user breathes through the gas measurement component and the oxygen delivery housing; and
    (d) a tubular adapter piece comprising a base leg and two side legs in common communication, the tubular adapter in communication with a distal end of the gas measurement component, a first side leg having a check valve therein oriented to permit proximal flow and to prevent distal flow therethrough, the first side leg having a distal end in communication with a proximal end of the oxygen delivery housing, and a second side leg having a check valve therein oriented to permit distal flow and to prevent proximal flow therethrough, the second side leg having a distal end in communication with the ambient atmosphere.

15. The face mask assembly of claim 14, wherein the tubular adapter piece is configured as at least one of a Y and a T.

16. A face mask assembly, comprising:
    a face mask sized and configured to substantially conformally fit over the oral and nasal region of a patient's face, the mask having a port;

a gas measurement component having a proximal end operably coupled to the face mask through the port and arranged as a mainstream adapter; and an oxygen delivery housing in communication with a distal end of the gas measurement component, the oxygen delivery housing defining an adjustable volume reservoir and including an oxygen delivery inlet port opening into the housing and a primary fluid flow port opening into the housing.

17. A face mask assembly, comprising:

a face mask sized and configured to substantially conformally fit over the oral and nasal region of a patient's face, the mask having a port;

a gas measurement component having a proximal end operably coupled to the face mask through the port and arranged as a mainstream adapter;

an oxygen delivery housing in communication with a distal end of the gas measurement component, the oxygen delivery housing defining an adjustable volume reservoir and including an oxygen delivery inlet port opening into the housing and a primary fluid flow port opening into the housing; and a tubular adapter piece comprising a base leg and two side legs in common communication, the tubular adapter in communication with a distal end of the gas measurement component, a first side leg having a check valve therein oriented to permit proximal flow and to prevent distal flow therethrough, the first side leg having a distal end in communication with a proximal end of the oxygen delivery housing, and a second side leg having a check valve therein oriented to permit distal flow and to prevent proximal flow therethrough, the second side leg having a distal end in communication with the ambient atmosphere.

* * * * *